United States Patent [19]

Kazlauskas et al.

[11] Patent Number: 5,959,159
[45] Date of Patent: Sep. 28, 1999

[54] METHOD FOR PREPARING OPTICALLY ACTIVE 5-HYDROXY-3-(4'-HYDROXYPHENYL)-1,1,3-TRIMETHYLINDANE

[75] Inventors: Romas Joseph Kazlauskas; Xiaoming Zhang, both of Montreal, Canada

[73] Assignee: Molecular OptoElectronics Corporation, Watervliet, N.Y.

[21] Appl. No.: 08/957,524

[22] Filed: Oct. 24, 1997

[51] Int. Cl.[6] .................... C07C 37/11; C07C 37/20; C07C 39/12; C12N 9/18
[52] U.S. Cl. .................... 568/719; 568/721; 568/727; 568/732; 568/734; 435/197
[58] Field of Search ................ 568/719, 721, 568/727, 732, 734, 736; 528/74, 190; 435/18, 197, 822

[56] References Cited

U.S. PATENT DOCUMENTS

| | | | |
|---|---|---|---|
| 2,979,534 | 4/1961 | Petsopoulas et al. | 260/619 |
| 4,334,106 | 6/1982 | Dai | 568/719 |
| 4,879,421 | 11/1989 | Kazlauskas | 568/737 |
| 5,703,197 | 12/1997 | Gordon et al. | 528/201 |
| 5,777,063 | 7/1998 | Gordon et al. | 528/74 |

OTHER PUBLICATIONS

Lang et al., "Crystal Structure of a Bacterial Lipase from Chromobacterium viscosum ATCC 6918 Refined at 1.6 A Resolution", J. Mol. Biol. 259, 704–717 (1996).

K. Laumen and M. Schneider, "A Facile Chemoenzymatic Route to Optically Pure Building Blocks for Cyclopentanoid Natural Products", J. Chem. Soc., Chem. Commun. 1298–1299 (1986).

*Primary Examiner*—Shailendra Kumar
*Assistant Examiner*—Sreeni Padmanabhan
*Attorney, Agent, or Firm*—Martha L. Boden, Esq.; Heslin & Rothenberg, P.C.

[57] ABSTRACT

A process for resolving racemic diesters of (R,S)(±)-5-hydroxy-3-(4'-hydroxyphenyl)-1,1,3-trimethylindane is disclosed. The process utilizes a microbial enzyme derived from *Chromobacterium viscosum* to catalyze the enantioselective and regioselective hydrolysis of the (S)(−)-enantiomer of the racemic mixture to its corresponding monoester at a faster rate than the (R)(+)-enantiomer. A substantially pure (S)(−)-indane monoester is thereby formed, while the (R)(+)-indane diester remains unreacted. The (S)(−)-monoester and the (R)(+)-diester can then be hydrolyzed using conventional techniques to form optically active (R)(+)- and (S)(−)-5-hydroxy-3-(4'-hydroxyphenyl)-1,1,3-trimethylindane enantiomers for use as monomers in the synthesis of chiral polymers.

7 Claims, No Drawings

METHOD FOR PREPARING OPTICALLY ACTIVE 5-HYDROXY-3-(4'-HYDROXYPHENYL)-1,1,3-TRIMETHYLINDANE

The following invention was made with Government support under contract number F33615-95-C-5432 awarded by the United States Air Force. The Government has certain rights in this invention.

FIELD OF THE INVENTION

The present invention relates to a process for preparing substantially pure enantiomers of 5-hydroxy-3-(4'-hydroxyphenyl)-1,1,3-trimethylindane. The invention also relates to a process for resolving a racemic mixture of diester derivatives of (R,S)(±)-5-hydroxy-3-(4'-hydroxyphenyl)-1,1,3-trimethylindane by the enantioselective and regioselective hydrolysis of one diester in the racemic mixture using a microbial lipase derived from *Chromobacterium viscosum*.

BACKGROUND OF THE INVENTION

Optically active enantiomers of 5-hydroxy-3-(4'-hydroxyphenyl)-1,1,3-trimethylindane (also referred to herein as "indane bisphenol") represented by the formula

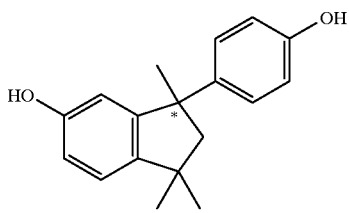

wherein the asterisk (*) used herein represents the single chiral center, have utility as monomers in the chemical synthesis of various chiral polymers. For example, chiral polycarbonates, polyesters, polyurethanes, and polyethers synthesized from optically pure chiral indane bisphenol monomers are disclosed in two commonly assigned U.S. patent applications being filed concurrently herewith and corresponding respectively to Docket Nos. 0953.032 and 0953.028. These optically pure polymers are useful in the fabrication of optoelectronics devices such as chiral waveguides and/or optical materials such as polarizing coatings and filters. Thus, a need exists for a convenient method for producing optically pure enantiomers of indane bisphenol from racemic indane bisphenol.

HPLC methods using columns packed with a chiral stationary phase are frequently employed to separate enantiomers. However, such methods are typically analytical techniques and can often be difficult and expensive to scale up and perform on a commercial scale. Other traditional separation methods, such as fractional crystallization, are often tedious and expensive, and processing problems are frequently encountered in the preparation of enantiomers on a synthetic scale.

Another method often used to resolve racemic mixtures of chiral compounds involves subjecting the mixture to the stereoselective action of various enzymes. Generally, enzymes for use in resolutions should exhibit a high degree of stereoselectivity for catalyzing the reaction of one isomer to the exclusion of others. For example, enzymatic resolution by enantioselective hydrolysis of various ester compounds has been widely employed for the lab-scale, preparative-scale, and industrial-scale production of many optically pure esters.

One class of enzymes, the hydrolases, which includes lipases, proteases, esterases, trypsins, chymotrypsins, and dextranases, for example, is often used in the resolution of enantiomers because they are commercially available at reasonable cost, they do not require expensive cofactors, and some exhibit reasonable tolerance to organic solvents. Additionally, hydrolases are known to catalyze enantioselective hydrolysis of esters. However, one disadvantage of enzyme-catalyzed resolution processes, including those catalyzed by hydrolases, is that there is no way to predict in advance the stereospecificity of a certain genus of enzyme for a given substrate.

Resolution of the enantiomers of the racemic esters of (R,S)(±)-indane bisphenol using any of the aforementioned methods has not heretofore been described. Such a resolution is desirable to prepare substantially pure indane bisphenol enantiomers for use as monomers in the synthesis of chiral polymers. Such chiral polymers are useful in the manufacture of high performance optical materials. A definite need therefore exists for a convenient, economic, and efficient method for separating the individual enantiomers of racemic (R,S)(±)-indane esters to produce on a commercial scale optically active indane bisphenol isomers.

SUMMARY OF THE INVENTION

As a result of various studies, it has now been unexpectedly found that optically active 5-hydroxy-3-(4'-hydroxyphenyl)-1,1,3-trimethylindane can be conveniently prepared in high enantiomeric purity by lipase-catalyzed hydrolysis of diesters of the corresponding racemate. The resolution process of the present invention is accomplished through the use of a microbial lipase derived from *Chromobacterium viscosum* that stereoselectively catalyzes hydrolysis of the (S)(−)-indane diester at a faster rate than the (R)(+)-indane diester. In addition, the lipase regioselectively hydrolyzes the ester group on the more substituted phenyl group to form a substantially pure (S)(−)-4'-indane monoester, while the diester of (R)(+)-indane bisphenol remains unreacted. After separation, the (R)(+)-indane diester and (S)(−)-4'-indane monoester can then be individually hydrolyzed by conventional methods to produce optically active (S)(−)-indane bisphenol and optically active (R)(+)-indane bisphenol. As used herein, the terms "indane diester" and "indane monoester" refer to esters prepared from indane bisphenol.

In accordance with the present invention, a method is therefore provided for preparing a substantially pure enantiomer by resolving a mixture of indane diester enantiomers. The process comprises the steps of:

(a) providing an organic phase comprising a mixture of (R,S)(±)-indane diester enantiomers represented by formula (I)

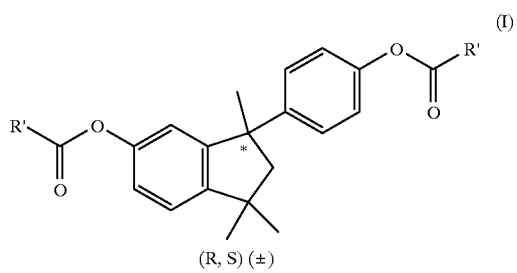

wherein R' is an alkyl group, alkenyl group, a 5 or 6 membered heterocyclic group having an oxygen atom or nitrogen atom as a hetero atom, or deuterated equivalents thereof, and * indicates a chiral carbon;

(b) contacting the organic phase with an aqueous solution comprising water and a catalytic amount of a microbial lipase derived from *Chromobacterium viscosum* to form a mixture comprising (S)(−)-4'-indane monoester represented by formula (II)

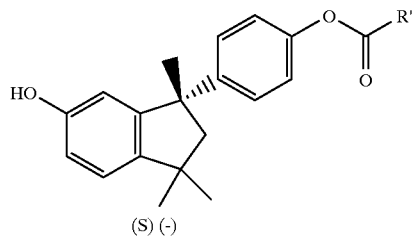

and (R)(+)-indane diester of formula (III)

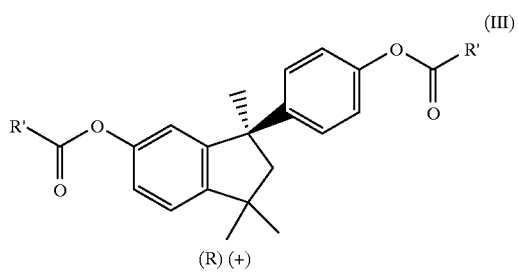

and c) separating the (R)(+)-indane diester (III) from the (S)(−)-4'-indane monoester (II).

Steps (a) and (b) are depicted by the following scheme:

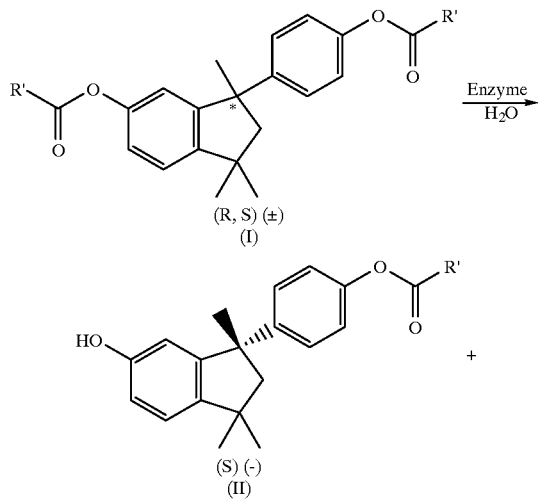

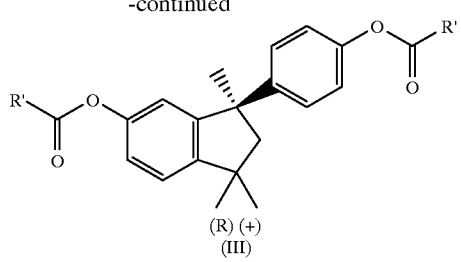

After separation, the (R)(+)-indane diester enantiomer represented as formula (III) above can then be hydrolyzed to form substantially pure (R)(+)-5-hydroxy-3-(4'-hydroxyphenyl)-1,1,3-trimethylindane. Likewise, the (S)(−)-indane monoester enantiomer (II) can be hydrolyzed to form substantially pure (S)(−)-5-hydroxy-3-(4'-hydroxyphenyl)-1,1,3-trimethylindane.

The lipase derived from *Chromobacterium viscosum* is water soluble, whereas the diesters of the present invention exhibit very low solubilities in water. Therefore, the enzyme-mediated optical resolution may be conducted under two-phase or multiphase reaction conditions. Preferably, the aqueous solution is maintained at a pH in the range of about 4 to 9, and the reaction occurs at a temperature from about 5° C. to about 50° C. In a preferred embodiment, the R' group of formulas (I), (II), and (III) is a propyl or butyl group.

DETAILED DESCRIPTION OF THE INVENTION

The present invention provides a method for the production of substantially pure enantiomers of 5-hydroxy-3-(4'-hydroxyphenyl)-1,1,3-trimethylindane, subsequently useful as monomers in the synthesis of optically active polymers. Specifically, this invention relates to the production of enantiomers of indane bisphenol by a process of enzymatic stereoselective and regioselective hydrolysis. Racemic (R,S)(±)-indane diester mixtures (I), typically prepared from racemic (R,S)(±)-5-hydroxy-3-(4'-hydroxyphenyl)-1,1,3-trimethylindane, are resolved by contacting the diester racemate with a lipase derived from *Chromobacterium viscosum*. The resolution process described herein is a kinetic resolution process in which each enantiomer of the racemic substrate mixture exhibits some susceptibility to enzymatic hydrolysis, but the (S)(−)-diester enantiomer is hydrolyzed at a faster rate than the (R)(+)-diester. In addition, the ester located on the more substituted phenyl group (at the 5 position) is preferentially hydrolyzed over that located on the less substituted phenyl group (at the 4' position). If the hydrolytic process is terminated at the proper point, (S)(−)-4'-indane monoester is produced, while the (R)(+)-indane diester remains essentially unreacted.

Separation using conventional column chromatography techniques yields an enantiomerically enriched (S)(−)-4'-indane monoester (II), and an enantiomerically enriched (R)(+)-indane diester (III). Commonly known hydrolysis methods can then be used to hydrolyze the (S)(−)-4'-monoester and (R)(+)-diester providing substantially pure (S)(−)-5-hydroxy-3-(4'-hydroxyphenyl)-1,1,3-trimethylindane and substantially pure (R)(+)-5-hydroxy-3-(4'-hydroxyphenyl)-1,1,3-trimethylindane, respectively. As used here in, "substantially pure" refers to a product having an ee greater than 85%, but preferably greater than 95%.

The ability of an enzyme to discriminate between two competitively reacting enantiomers may be quantified by the enantioselectivity value E, as described by C. S. Chen et al. in *J. Amer. Chem. Soc.* 104, 7294–99 (1982). The formula for calculation of E in the case of a subtractive kinetic resolution process, such as ab→a+b, is given as follows:

$$E = \ln[(1-c(1+ee(a)))]/\ln[(1-c(1-ee(a))]$$

where c is the extent of conversion of the entire quantity of starting racemic substrate ab, expressed as a decimal fraction, and ee(a) is the enantiomeric excess of the hydrolyzed product enantiomer, also expressed as a decimal fraction. This formula permits comparison of enzyme reactions which have proceeded to different degrees of conversion, in which case direct comparison of the enantiomeric excess of the remaining diester substrate is not meaningful. It is also possible to use this E value and corresponding calculations to compare the apparent selectivity of the same enzyme operating under varying conditions.

Based on the above equation, the % enantiomeric excess (%ee(a)) for the non-hydrolyzed substrate enantiomer is calculated by the following equation:

$$\%ee(a) = \{(\text{conc. of } a - \text{conc. of } b)/(\text{conc. of } a + \text{conc. of } b)\} \times 100\%$$

Enantiomeric excess is related to the older term "optical purity" in that both are measures of the same phenomenon. The value of %ee will be a percentage from 0 to 100%, zero being racemic and 100 being a pure, single enantiomer.

In the resolution process of the present invention, an infinitely large E value displayed by the enzyme would be ideal. In the perfect case (E=∞), at 50hydrolysis of the total starting racemic substrate, 100% of the non-hydrolyzed material will remain after reaction at an optical purity of 100% enantiomeric excess (%ee(a)=100). However, since real-world enzymes generally display an E value below ∞, the overall extent of hydrolysis must be allowed to proceed past 50%, to an extent that is determined by the formula derived by Chen et al. and reproduced above. Generally, an E value of at least 25 is necessary for a process to be of commercial value.

Preferably, the enzyme catalyst will be chosen to display the largest E value possible, thus permitting recovery of the greatest amounts of both the non-hydrolyzed (R)(+)-indane diester enantiomer and the hydrolyzed (S)(−)-4'-indane monoester for a given degree of enantiomeric excess. The lipase derived from *Chromobacterium viscosum* (or, as discussed below, the lipase derived from *Pseudomonas glumae*) has been surprisingly found to be (S)(−)-selective with a relatively large E value. In addition, as determined by $^{1}$H-NMR, the hydrolysis process is regioselective with respect to the position of the esters in the racemic indane diester, and hydrolysis proceeds preferentially at the 5-position of the diester compound, i.e. at the ester on the more substituted phenyl ring, while the ester on the less substituted phenyl ring (4'-position) remains virtually unreacted.

It should be noted that Lang et al. report in *J. Mol. Bio.* 259, 704–717 (1996) that the lipase derived from *Chromobacterium viscosum* has the same sequence as the *Pseudomonas glumae* lipase with the exception of three amino acids in *Chromobacterium viscosum*. Thus, catalytic hydrolysis of the racemic (R,S)(±)-indane diester (I) by the lipase derived from *Pseudomonas glumae* should also result in a mixture of (S)(−)-4'-indane monoester of formula (II) and (R)(+)-indane diester having formula (III). The present invention is therefore not limited to the use of the lipase derived from *Chromobacterium viscosum*, but also includes the lipase derived from *Pseudomonas glumae*. As used herein, the phrase "lipase derived from *Chromobacterium viscosum*" means either the lipase derived from *Chromobacterium viscosum* or the lipase derived from *Pseudomonas glumae*.

Racemic (R,S)(±)-indane bisphenol for use in the practice of this invention can be prepared according to the method disclosed in U.S. Pat. No. 4,334,106 by treating iso-propenyl phenol (IPP) or a mixture of its linear oligomers with a stoichiometric excess of organic acid. IPP can be prepared by base catalyzed cracking of BPA. The disclosure of U.S. Pat. No. 4,334,106 is incorporated herein by reference. Alternatively, racemic (R,S)(±)-indane bisphenol can be prepared by reacting the corresponding indanamine with sodium nitrite in the presence of aqueous acid as described by J. C. Wilson, *Journal of Polymer Science: Polymer Chemistry Edition* 13, 749 (1975), which is incorporated herein by reference. Also, see U.S. Pat. No. 2,979,534, which is also incorporated herein by reference. The indanamine can be prepared by the method described by J. C. Petropoulos and J. J. Fisher, *J. Amer. Chem. Soc.* 80, 1938 (1958) from the corresponding carboxy indane compound, which is also incorporated herein by reference.

Racemic (R,S)(±)-indane diesters of formula (I) can be prepared by any known method, for example, by the reaction of racemic indane bisphenol with triethylamine and an appropriate acid chloride or anyhdride in a suitable solvent such as tetrahydrofuran or ethyl ether.

The substituent group defined as R' in the representative formulas (I), (II), and (III) can be an alkyl group, alkenyl group, a 5 or 6 membered heterocyclic group having an oxygen atom or nitrogen atom as a hetero atom, such as tetrahydropyranyl or pyrimidyl, or deuterated equivalents thereof. As used herein, "alkyl" refers to saturated linear, branched and cyclic hydrocarbon residues containing 20 or fewer carbons. "Alkenyl" refers to linear, branched, or cyclic unsaturated hydrocarbons containing up to 20 carbons and having at least one double bond. "Deuterated equivalents thereof", as used herein, refers to the hydrocarbon moieties listed above for R' in which at least one hydrogen is replaced with the deuterium isotope. For example, a deuterated methyl group may be $CDH_2$, $CD_2H$, or $CD_3$, and a deuterated ethyl may be $CH_3CD_2$. For purposes of the present invention, R' is preferably a straight chain alkyl group, and most preferably propyl or butyl.

Because the racemic lower alkyl indane diesters (I) are oils at room temperature that emulsify into a second (organic) phase upon addition of an aqueous solution, these racemic diester mixtures may be used in the present invention without addition of an organic solvent. Alternatively, racemic indane diester (I) may be dissolved in an organic solvent to form an organic phase which is separable from aqueous solution. The selected organic solvent is one which is appreciably immiscible with water, such as hexane, heptane, methyl isobutyl ketone, t-butyl methyl ether, butanol, toluene, ethyl acetate, or methylene chloride. However, the invention is not limited to the use of the above-mentioned solvents, and other suitable water immiscible organic solvents that may be used will be obvious to those skilled in the art. As used herein, the term "immiscible" refers to liquids that cannot be uniformly mixed in all proportions, and "water immiscible" includes solvents which are completely, substantially, or partially immiscible with water-i.e. solvents such as butanol that form a separate organic phase when placed in contact with water.

The enzyme catalyst derived from *Chromobacterium viscosum* for use in the present invention may be obtained as a lyophilized powder and subsequently dissolved in water or in an aqueous buffering solution, such as phosphate. While highly purified enzyme preparations are not necessary for the process of this invention, if the enzyme to be used herein has intrinsically low specific activity units (units of catalytic activity per weight of protein), crude preparations thereof can cause practical problems by requiring unnecessarily large volumes of reaction mixtures and correspondingly large reactor volumes.

*Chromobacterium viscosum* lipase for use in the present invention may be obtained from any convenient source and is commercially available from Sigma (U.S.), Asahi (Japan), Biocatalyst (U.K.), Amresco (U.S.), and Genzyme (U.S.), for example. Alternatively, the lipase may be prepared from *Chromobacterium viscosum*, which is available from American Type Culture Collection (ATCC 6918). Briefly, *Chromobacterium viscosum* (as well as *Pseudomonas gulmae*) produces a lipase that may be obtained by extraction from cultured broths of the microorganisms, followed by purifying the extract by a conventional method. In addition, the bacteria may be either wild type or mutants. Recombinant strains derived using genetic means such as cell fusion or genetic engineering may also be used. The medium for cultivating *Chromobacterium viscosum* (or *Pseudomonas glumae*) for use in the present invention may be any medium on which the microorganisms will grow. For example, an ordinary liquid nutrient medium containing carbon sources, nitrogen sources, inorganic salts and organic nutrients may be used.

The concentration of the racemic (R,S)(±)-indane diester mixture to be hydrolyzed is not critical. Similarly, the concentration of lipase required to effect hydrolysis of the (S)(−)-diester is not critical to the practice of this invention. However, in preferred embodiments, the enzyme concentration will be an amount which is effective to achieve hydrolysis in a reasonable period of time (i.e. several hours to several days) and may depend on the purity of the enzyme. Such an effective amount is referred to herein as a "catalytic amount".

The pH of the reaction medium is also not critical to the process of this invention and may vary from about 4 to 9, which covers the pH optimum for the *Chromobacterium viscosum* preparation in use. It is desirable to maintain the pH of the aqueous phase within the desired range over the course of the hydrolysis by use of a buffer system. Examples of buffers with buffering capacity over the desired range include, but are not limited to, carbonates, bicarbonates, phosphates, borates, and citrates. Additionally, an automatic titrator using NaOH as the titrant, for example, or other pH controlling device may be used.

Similarly, the temperature at which the hydrolysis is performed may vary over a wide range provided that both the aqueous and organic phases remain liquid, the enzyme does not experience denaturation at a rate too rapid to allow its use, and the esters remain stable; preferably the temperature is between about 5°–50° C. The relative volumes of the aqueous and organic phases are not critical, and may vary over a wide range. In the preferred embodiments of the present invention, the temperature, the pH of the aqueous phase, the concentration of the enzyme from *Chromobacterium viscosum* in the aqueous phase, and the concentration of the racemic indane diester compound are chosen such that an optimal combination of rate and enantioselectivity of hydrolysis is realized.

The lipase-catalyzed hydrolysis reaction is conducted by contacting the racemic indane diester-containing organic phase with the aqueous phase in the presence of the *Chromobacterium viscosum* lipase using conventional stirring or shaking techniques. Alternatively, known methods wherein the enzymatic resolution process is conducted within a multi-phase/extractive enzyme membrane reactor may be employed. An example of such a membrane reactor may be found in U.S. Pat. No. 5,077,217 (Matson et al.), the disclosure of which is incorporated by reference.

Since the racemic (R,S)(±)-indane diester mixture (I), the (S)(−)-4'-indane monoester (II), and the (R)(+)-indane diester (III) are preferentially soluble in the organic phase, and nearly insoluble in the aqueous phase, the esters will remain in the organic phase after hydrolysis. The aqueous solution will contain the enzyme.

The progress of the lipase-catalyzed asymmetric hydrolysis may be conveniently monitored by periodic HPLC analyses of the reaction mixture until the desired extent of conversion is reached. After completion of the hydrolysis, the substantially pure (S)(−)-4'-indane monoester enantiomer (II) is then separated from the (R)(+)-indane diester (III) enantiomer, preferably by column chromatography.

The substantially unreacted (R)(+)-diester can then be saponified to form substantially pure (R)(+)-5-hydroxy-3-(4'-hydroxyphenyl)-1,1,3-trimethylindane by methods well-known in the art. For example, sodium methoxide can be added to the unreacted (R)(+)-indane diester in methanol and stirred, followed by extraction with ethyl acetate. Evaporation of the combined extracts yields a white powder, and recrystallization from methanol-water yields crystals of ±-indane bisphenol leaving a methanol/water solution enriched in (R)(+)-indane bisphenol. Evaporation and recrystallization of the solid from methanol-dichloromethane provides crystalline (R)(+)-indane bisphenol.

Alternatively, the unreacted (R)(+)-diester may be hydrolyzed by refluxing the (R)(+)-diester in water or dilute aqueous acids. The (R)(+)-indane bisphenol may also be prepared by treating the (R)(+)-diester with ammonia or dilute aqueous sodium or potassium hydroxide solution at elevated temperatures. In a similar manner, substantially pure (S)(−)-5-hydroxy-3-(4'-hydroxyphenyl)-1,1,3-trimethylindane can be prepared by hydrolyzing the (S)(−)-4'-monoester using conventional techniques, such as those described above.

The present invention is more particularly described and explained by means of the following detailed Examples of preferred embodiments. It is to be understood, however, that such Examples are for illustration purposes only and are not intended to limit the scope of the present invention.

EXAMPLE 1

Preparation of Racemic (R,S) (+,−)-Indane Diesters of Formula (I)

An appropriate acid chloride (8.9 mmol., 2.4 eq.) dissolved in dried tetrahydrofuran (THF) (25 mL) was added over a period of 10 min. to a solution of racemic (R,S)(±)-indane bisphenol (1.0 g, 3.7 mmol) and triethylamine (0.905 g, 8.94 mmol, 2.4 eq.) in dried THF (25 mL). The reaction was stirred overnight at room temperature. Analysis by thin layer chromatography (silica gel eluted with dichloromethane:hexane (8:2) and visualized by uv) indicated that diesterification was complete. Fifty mL of 10% HCl solution was added to the reaction mixture. The mixture was extracted three times with 20 mL of ethyl acetate. The diester was isolated by washing the combined extracts with 10% $NaHCO_3$ (three times, 20 mL) and water (two times, 20 mL), followed by drying over magnesium sulfate (10 g). Column chromatography on silica gel eluted with dichloromethane yielded the respective racemic (R,S)(±)-indane diester (diacetate through didecanoate) as a colorless oil in 90–95% yield. The racemic (R,S)(±)-indane diesters produced were characterized by $^1$H- and $^{13}$C-NMR spectroscopy and by mass spectrometry.

EXAMPLE 2

Structural Determination of (S)(−)-4'-Indane Monoesters

Based on comparison of the $^1$H-NMR chemical shifts of the aromatic protons of indane and those of (R)(+)-indane dipentanoate, and (S)(−)-indane monopentanoate isolated from the *Chromobacterium viscosum* lipase-catalyzed hydrolysis of indane dipentanoate, the ester group on the more substituted phenyl group was determined to be preferentially hydrolyzed. All the aromatic protons in the indane bisphenol resonate 0.2–0.3 ppm upfield of those in indane dipentanoate. In the monopentanoate, the resonances of the hydrogens on the more substituted ring lie 0.15–0.27 ppm upfield from those in the indane dipentanoate, while the hydrogen resonances of the less substituted ring lie within 0.01 ppm of those corresponding to the dipentanoate. Thus, after hydrolysis, the ester group lies on the less substituted ring, and *Chromobacterium viscosum* lipase favors hydrolysis of the ester on the more substituted ring to form (S)(−)-4'-indane monoester (II).

EXAMPLE 3

*Chromobacterium Viscosum* Lipase Catalyzed Enantiospecific and Regiospecific Hydrolysis of Racemic (R,S)(+,−)-Indane Dibutyrate Preparation of Racemic (R,S)(+,−)-Indane Dibutyrate A solution of 21.8 g (0.081 mol) of racemic (R,S)(±)-indane bisphenol and 19.7 g (0.19 mol) of triethylamine in 500 mL of THF was magnetically stirred in a 4L round-bottom flask. The flask was cooled in an ice water bath, and 21 g (0.19 mol) of butyryl chloride were added over 20 min. The flask was removed from the ice water bath and stirred for one hour to ensure complete reaction. 300 mL of 10% HCl solution was added to the reaction mixture, and the mixture was extracted 3 times with 200 mL ethyl acetate. The combined organic phases were concentrated to 200 mL and poured into a 1L separatory funnel and washed twice with 150 mL portions of 1 M sodium bicarbonate and once with a 160 mL portion of water, resulting in a clear, slightly yellowish solution. The solution was dried over MgSO$_4$, filtered, and concentrated in vacuo yielding 32 g of crude racemic (R,S)(±)-indane dibutyrate.

Hydrolysis

In a 1L round-bottom flask, 32 g of racemic (R,S)(±)-indane butyrate was diluted to 240 mL with tert-butyl methyl ether. Phosphate buffer (240 mL, 0.1 M, pH 7.5) was added, and the mixture was stirred with a magnetic stirrer. The pH of the mixture was adjusted to 7.20 with 1 M sodium hydroxide. *Chromobacterium viscosum* lipase (20.4 mg of solid containing 65% protein and 6.060 units/mg protein (obtained from Sigma)) was dissolved in 15 mL phosphate buffer and added to the reaction flask. Stirring was continued, and the pH was maintained at 7.2±0.3 by addition of 1 M NaOH. The reaction rate was measured by the consumption of base. Approximately 19 mL of base were consumed in the first 3 hours, and an additional 15 mL were consumed over the next 2 hours. Thus, after 5 hours, approximately 34 mL of base had been consumed. The reaction was monitored by HPLC at 272 nm on a CHIRAL-CEL™ column, and the optical purity of the enantiomers determined using the equations provided by Chen et al. above. The extinction coefficients of the two enantiomers are equal.

After 5 hours, HPLC analysis indicated that the hydrolysis had reached 43% conversion, and that the ee of the (S)(−)-4'-indane monobutyrate was 92%. The reaction was then stopped by separation of the organic and aqueous phases using a separatory funnel. The aqueous phase was extracted with ethyl acetate (four times with 100 mL), followed by dichloromethane (three times with 100 mL). The aqueous phase containing enzyme was stored in a freezer for further use.

The organic phases were combined, then concentrated by rotary evaporation to a sticky gum. The gum was dissolved in dichloromethane (200 mL), then washed twice with 100 mL portions of 1 M sodium bicarbonate and three times with 100 mL portions of water, followed by drying over MgSO$_4$ (30 g). The solution was concentrated by rotary evaporation to a thick oil (30 g). The oil was chromatographed in three portions on a silica gel column, eluting with dichloromethane to recover non-hydrolyzed R)(+)-indane dibutyrate ($R_f$=0.84) and (S)(−)-4'-indane monobutyrate ($R_f$=0.24). A subsequent elution with ethyl acetate led to the recovery of an additional fraction of (S)(−)-4'-indane monobutyrate ($R_f$=1).

The oil fractions containing (S)(−)-4'-indane monobutyrate contained 9.3 g of the enantiomer (35% yield), as characterized by $^1$H- and $^{13}$C-NMR. The ee was 92%, and the observed optical rotation, $[\alpha]^D_{25}$, was −61.6 (c 3.85, MeOH). The fractions containing non-hydrolyzed (R)(+)-indane dibutyrate were concentrated providing 17.3 g (54% yield) of the enantiomer in 52% ee; $[\alpha]^D_{25}$=+59.3 (c 3.25, MeOH) The corresponding E value was 40, which was consistent with the values measured during enzymatic screening.

The results of the hydrolysis are summarized in the following TABLE.

TABLE

| Time (hr) | ee (%) (S)(−)- Monobutyrate | ee (%) (R)(+)- Dibutyrate | Conversion (%) | E |
|---|---|---|---|---|
| 5 | 92 | 52 | 43 | 40 |

(R)(+)-5-Hydroxy-3-(4'-Hydroxyphenyl)-1,1,3-Trimethylindane

To obtain (R)(+)-5-hydroxy-3-(4'-hydroxyphenyl)-1,1,3-trimethylindane, sodium methoxide (5.1 g of 95% powder, 2.2 eq.) was added to 15.7 g (0.038 mol) of the recovered (R)(+)-indane dibutyrate in methanol (300 mL), and the solution was stirred for 2 hours. The reaction mixture was neutralized to pH 7 with 1 M HCl and extracted three times with equal amounts of ethyl acetate (50 mL portions). Evaporation of the combined extracts yielded (R)(+)-indane bisphenol as a white powder (10.2 g, 100% yield, 52% ee). Recrystallization from methanol-water yielded crystals of (±)-indane bisphenol (2.1 g of 3% ee, 200 mg of 13% ee) leaving the solution enriched in (R)(+)-indane bisphenol (6.2% ee). Recrystallization from methanol-dichloromethane yielded crystalline (R)(+)-indane bisphenol (2.5 g) in >99% ee. The observed optical rotation, $[\alpha]^D_{25}$, was +105.2. The melting point was 152–158° C., compared with 203–206° C. for racemic (R,S)(±)-indane bisphenol.

(S)(-)-5-Hydroxy-3-(4'-Hydroxyphenyl)-1,1,3-Trimethylindane

To obtain (S)(-)-5-hydroxy-3-(4'-hydroxyphenyl)-1,1,3-trimethylindane, sodium methoxide (2.6 g of 95% powder, 1.1 eq.) is added to 8 g (0.022 mol) of the recovered (S)(-)-indane monobutyrate in methanol (300 mL), and the solution is stirred for 2 hours. The reaction mixture is neutralized to pH 7 with 1 M HCl and extracted three times with equal amounts of ethyl acetate (50 mL portions). Evaporation of the combined extracts followed by recrystallization yields (S)(-)-indane bisphenol.

While the invention has been particularly shown and described with reference to the preferred embodiments thereof, it will be understood by those skilled in the art that other changes in form and details may be made therein without departing from the spirit and scope of the invention.

We claim:

1. A method for preparing a substantially pure enantiomer comprising the steps of:

a) providing an organic phase comprising a mixture of (R,S)(±)-indane diester enantiomers, said enantiomers represented by formula (I)

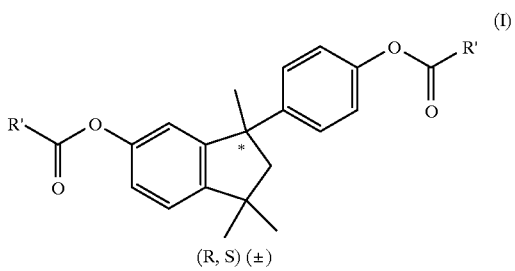

wherein R' is an alkyl group, alkenyl group, a 5 or 6 membered heterocyclic group having an oxygen atom or nitrogen atom as a hetero atom, or deuterated equivalents thereof, and * indicates a chiral carbon;

b) contacting said organic phase with an aqueous solution comprising water and a catalytic amount of a microbial lipase derived from *Chromobacterium viscosum* to form a mixture comprising (S)(-)-4'-indane monoester represented by formula (II)

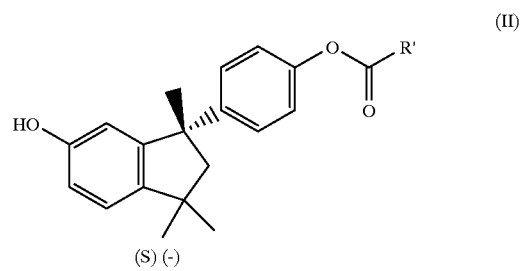

and (R)(+)-indane diester of formula (III)

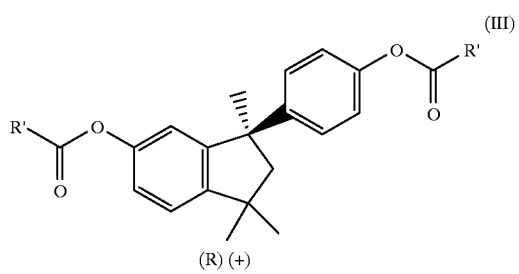

and c) separating said (R)(+)-indane diester from said (S)(-)-4'-indane monoester.

2. The method according to claim 1 further comprising the step of hydrolyzing said (R)(+)-indane diester to form substantially pure (R)(+)-5-hydroxy-3(4'-hydroxyphenyl)-1,1,3-trimethylindane.

3. The method according to claim 1 further comprising the step of hydrolyzing said (S)(-)-indane monoester to form substantially pure (S)(-)-5-hydroxy-3-(4'-hydroxyphenyl)-1,1,3-trimethylindane.

4. The method according to claim 1, wherein said organic phase further comprises a water immiscible organic solvent.

5. The method according to claim 1, wherein R' is a propyl or butyl group.

6. The method according to claim 1, wherein said aqueous solution is maintained at a pH in the range of about 4 to 9.

7. The method according to claim 1, wherein said contacting step occurs at a temperature from about 5° C. to about 50° C.

* * * * *